(12) United States Patent
Erdelmeier et al.

(10) Patent No.: US 8,309,763 B2
(45) Date of Patent: Nov. 13, 2012

(54) PROCESS FOR PREPARING 2-HYDROXY-4-METHYLSELENOBUTYRIC ACID, ALONE OR AS A MIXTURE WITH ITS SULPHUR-CONTAINING ANALOGUE, AND USES THEREOF IN NUTRITION, IN PARTICULAR ANIMAL NUTRITION

(75) Inventors: Irène Erdelmeier, Paris (FR); Marc Moutet, Cachan (FR)

(73) Assignee: Tetrahedron, Vincennes (FR)

( * ) Notice: Subject to any disclaimer, the term of this patent is extended or adjusted under 35 U.S.C. 154(b) by 599 days.

(21) Appl. No.: 12/312,024

(22) PCT Filed: Oct. 26, 2007

(86) PCT No.: PCT/EP2007/061567
§ 371 (c)(1),
(2), (4) Date: Oct. 15, 2009

(87) PCT Pub. No.: WO2008/049927
PCT Pub. Date: May 2, 2008

(65) Prior Publication Data
US 2010/0055291 A1     Mar. 4, 2010

(30) Foreign Application Priority Data

Oct. 27, 2006   (FR) ...................................... 06 09451

(51) Int. Cl.
*C07C 59/00*     (2006.01)
(52) U.S. Cl. ...................................................... 562/579
(58) Field of Classification Search ........................ None
See application file for complete search history.

(56) References Cited

U.S. PATENT DOCUMENTS 7,381,416 B2 *   6/2008   Erdelmeir et al. ............ 424/401

FOREIGN PATENT DOCUMENTS

FR          2 873 376         1/2006
WO      WO 96/36598 A1    11/1996

OTHER PUBLICATIONS

International Search Report issued on Mar. 17, 2008 for application No. PCT/EP2007/061567.
French Search Report issued on May 16, 2007 for application No. FR 06/09451.
May, "Selenium-based pharmacological agents: an update," *Expert Opinion on Investigational Drugs*, vol. 11, No. 9, 2002, pp. 1261-1269.
Agenas, "The synthesis of selenium analogues to pantoic acid," *Arkiv for Kemi*, vol. 24, 1965, pp. 573-576.
Dieden et al., "Synthesis of 1, 1-Bis(seleno)-2-alkenes," *Synthesis*, Aug. 1988, pp. 616-619.

* cited by examiner

*Primary Examiner* — Karl J Puttlitz
(74) *Attorney, Agent, or Firm* — Foley & Lardner LLP

(57) ABSTRACT

The present invention relates to a novel process for preparing 2-hydroxy-4-methylselenobutyric acid from 3-methylselenoproprion-aldehyde. The 2-hydroxy-4-methylselenobutyric acid is obtained alone or as a mixture with its sulphur-containing analogue. The invention also relates to the compositions, in particular nutritional compositions, comprising a mixture of 2-hydroxy-4-methylselenobutyric acid and 2-hydroxy-4-methylthiobutyric acid, and a physiologically acceptable medium, and to the use of this mixture as a dietary ingredient.

11 Claims, No Drawings

PROCESS FOR PREPARING 2-HYDROXY-4-METHYLSELENOBUTYRIC ACID, ALONE OR AS A MIXTURE WITH ITS SULPHUR-CONTAINING ANALOGUE, AND USES THEREOF IN NUTRITION, IN PARTICULAR ANIMAL NUTRITION

The present invention relates to a method for preparing 2-hydroxy-4-methylselenobutyric acid, alone or as a mixture with its sulphur-containing analogue, as well as uses thereof in nutrition, in particular in animal nutrition.

Selenium is an essential micronutrient for mammals and notably for humans. It is involved, as L(+)-selenocysteine or L(+)-selenomethionine, in the biosynthesis of selenoproteins such as glutathione peroxidase, thioredoxin reductase and selenoprotein P. According to the FDA-RDAs, the daily selenium needs in humans vary from 10-30 µg for children, to 40-70 µg for adolescents-adults, these levels being particularly high in women during pregnancy (65 µg/day) and lactation (75 µg/day). L(+)-selenomethionine complementation (2.7 µmol of selenium equivalent) in nursing women substantially increases selenium concentration in their milk.

In a certain number of situations such as deficiencies, diseases or exposure to radiations, a nutritional selenium complementation has proved to be very beneficial. This is most particularly true in the case of children affected by genetic diseases, such as phenylketonuria or hyperphenylalaninemia, which are subject to diets with low protein levels. In another field, selenium associated with vitamins, in organic form such as L(+)-selenomethionine has protective effects towards UV radiations in humans. Finally L(+)-selenomethionine protects from deleterious biological effects of high energy ionizing radiations.

A French patent application in the name of the applicant (FR 2 873376) reports for the first time 2-hydroxy-4-methylselenobutyric acid and its derivatives as well as their syntheses. Moreover, its sulphur-containing analog, 2-hydroxy-4-methylthiobutyric acid, also called liquid methionine, is known as a precursor of methionine for animal feeding (WO 9636598). It is made industrially for this application at a scale of several hundred thousand tons per year.

2-hydroxy-4-methylselenobutyric acid, a precursor of L(+)-selenomethionine, as well as 2-hydroxy-4-methylthiobutyric acid, a precursor of L(+)-selenomethionine, are therefore compounds of major interest in animal nutrition. It is therefore important to be able to have easily industrializable synthesis methods available, i.e. which may be carried out at a large scale, in the simplest way, the application and cost of which do not represent major handicaps.

The applicant has developed a synthesis method which meets these criteria and which has many advantages over the existing methods.

Thus, in a first aspect, the present invention relates to a method for preparing 2-hydroxy-4-methylselenobutyric acid, characterized in that it comprises the steps of:

reacting 3-methylselenopropionaldehyde of formula (I):

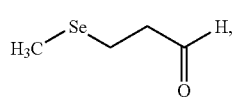

(I)

with an alkaline cyanide of formula $M^+CN^-$, preferably in the presence of an alkaline bisulphite salt of formula $M^+HSO_3^-$, M representing an alkaline metal atom, in a polar protic solvent, in order to lead to 2-hydroxy-4-methylselenobutyronitrile, a compound of formula (II):

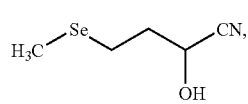

(II)

a compound of formula (II) which is hydrolyzed in a hot concentrated strong acid medium, in a polar protic solvent, in order to lead to the expected compound of formula (IV):

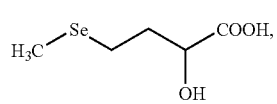

(IV)

which may optionally be transformed into one of its salts after addition with a physiologically acceptable base.

In an alternative of the method described earlier, the compound of formula (II) is hydrolyzed in a hot concentrated sulphuric acid medium in a polar protic solvent, in order to lead to a compound of formula (III):

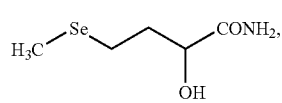

(III)

a compound of formula (III) which is itself hydrolyzed in a hot concentrated strong acid medium in order to lead to the compound of formula (IV).

According to an advantageous embodiment of the method according to the invention, the alkaline cyanide reagent is selected from sodium cyanide, potassium cyanide, and lithium cyanide.

One operates within a protic polar solvent such as for example water.

The subsequent reactions, with which the compound of formula (IV) may be transformed into its corresponding salts, are carried out under standard conditions known to one skilled in the art.

The method according to the present invention has the advantage of neither requiring complex reagents such as organometallic compounds, nor toxic agents such as alkylating agents, as in the methods from the prior art (FR 2 573 376). Further, it may be carried out at a large scale, in non-toxic solvents such as for example water. In addition to the feasibility aspect, these advantages also considerably reduce the application costs.

The compound of formula (I) which is used as a substrate for applying the method of the invention is known and how to obtain it is notably described in the publication, Synthesis, 1988, pages 616-619.

The benefit from the sulphur-containing analogue of the compound of formula (IV) above, 2-hydroxy-4-methylthiobutyric acid, is widely recognized (see above), in particular in the same field of nutrition. Simultaneous administration of this compound and of the compound of formula (IV) has an unquestionable advantage in terms of application and efficiency. In order to meet the needs of industrialization, it is important to be able to simply have both of these compounds in a mixture, and further with control over the relative proportion of both of these derivatives relatively to each other. Their administration, either simultaneously or separately, within formulations in defined proportions would also provide a significant advantage.

The applicant has shown that the preparation method according to the present invention and described earlier, may be used for simultaneously leading to a mixture of two sulphur-containing and selenium-containing compounds, which considerably improve industrial productivity.

Thus, in a second aspect, the present invention relates to a method for preparing a mixture of 2-hydroxy-4-methylselenobutyric acid and of 2-hydroxy-4-methylthiobutyric acid, in defined proportions, characterized in that it comprises the steps of:

reacting a mixture of 3-methylselenopropionaldehyde of formula (I), and of 3-methylthioprionaldehyde of formula (Ia):

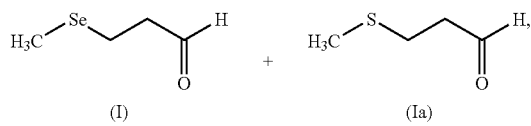

with an alkaline cyanide of formula $M^+CN^-$, preferably in the presence of an alkaline bisulphite salt of formula $M^+HSO_3^-$, M representing an alkaline metal atom, in a polar protic solvent, in order to lead to the mixture of 2-hydroxy-4-methylselenobutyronitrile of formula (II) and of 2-hydroxy-4-methylthiobutyronitrile of formula (IIa):

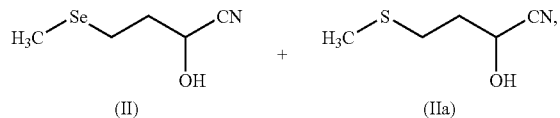

which, by hydrolysis in a hot strongly concentrated acid medium, in a polar protic solvent, leads to the mixture of the two compounds, the expected compounds of formulae (IV) and (IVa):

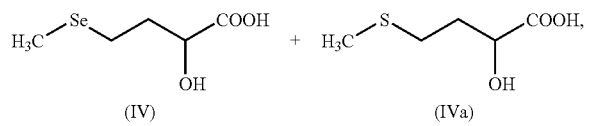

which may optionally be transformed into a mixture of their salts after addition with a physiologically acceptable base, it being understood that the relative proportions of both compounds (IV) and (IVa) are set from the beginning of the method, by the relative amounts of compounds (I) and (Ia) and are retained all along said preparation method.

In an advantageous aspect, the alkaline cyanide reagent is selected from sodium cyanide, potassium cyanide and lithium cyanide.

One operates within a protic polar solvent such as for example water.

In the method of the invention as described earlier, the relative proportion of the two compounds of formulae (IV) and (IVa) is controlled and may be adjusted depending on the contemplated application. In particular, the ratio between the compound (IV) and the compound (IVa) varies between 0.01% and 1% by weight, and preferentially between 0.05% and 0.5% by weight.

By simultaneously obtaining the compounds of formulae (IV) and (IVa), precursors of selenomethionine and of methionine, respectively, it is also possible to contemplate the preparation of compositions containing this mixture, since handling of them is simplified.

Thus, the object of the present invention is also a composition, in particular a nutritional composition comprising as an active ingredient, a mixture of 2-hydroxy-4-methylselenobutyric acid of formula (IV) and of 2-hydroxy-4-methylthiobutyric acid of formula (IVa), and a physiologically acceptable medium. The ratio between the compound (IV) and the compound (IVa) will in particular be comprised between 0.01% and 1.0% by weight and preferentially between 0.05% and 0.5% by weight.

By physiologically acceptable medium in the sense of the present invention, is meant a medium notably selected from:
an aqueous, alcoholic solution or an oil,
a water/oil or oil/water emulsion, a micro-emulsion,
an aqueous gel,
a dispersion of vesicles, microcapsules, microparticles or nanoparticles,
a solid medium consisting of one or more additives and/or excipients which may be selected from vitamins, natural antioxidants, mineral salts, mono-, di- or poly-saccharides, notably folic acid, vitamins $B_6$, E or C, lactose, starch. This solid medium consisting of one or more additives and/or excipients as defined above, and comprising at least one of the compounds of general formula (I), may be formulated as a gelatin capsule, a tablet or a powder. The amounts of the different constituents of these compositions, other than the compound of formula (IV) and (IVa) are those usually used for the mentioned applications.

As non-limiting examples simply given as an illustration, and which therefore cannot by any means limit the scope of the invention, these media may be nutritional liquids, such as for example food milk, fruit juices, syrups, but also milk for infants, or a parenteral solution, table salt, or generally any food complemented with selenium in a controlled way.

The invention also relates to the use of a mixture of 2-hydroxy-4-methylselenobutyric acid of formula (IV) and of 2-hydroxy-4-methylthiobutyric acid of formula (IVa) as a food ingredient, complement or additive.

The compound, 2-hydroxy-4-methylselenobutyronitrile, of formula (II):

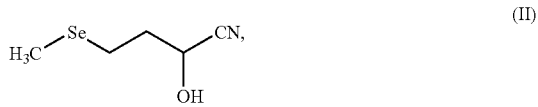

is novel, and as such, is part of the invention, as well as enantiomers thereof.

In the sense of the present invention, mineral bases such as sodium, lithium, calcium, potassium, magnesium, ammonium or zinc hydroxides, alkaline or earth alkaline metal carbonates such as sodium, lithium, calcium, potassium, magnesium, ammonium or zinc carbonates and bicarbonates, or organic bases such as methylamine, propylamine, trimethylamine, diethylamine, triethylamine, N,N-dimethylethanolamine, tris(hydroxymethyl)aminoethane, ethanolamine, pyridine, picoline, dicyclohexylamine, morpholine, proceine, lysine, arginine, histidine, N-methylglucamine, or further its phosphonium salts such as alkylphosphonium salts, arylphosphonium salts, arylalkylphosphonium salts, alkenylarylphosphoniums, or quaternary ammonium salts such as salts of tetra-n-butyl-ammonium, may be mentioned as a physiologically acceptable base, in a non-limiting way.

The compound of formula (II) is used within the scope of the present invention as a synthesis intermediate in obtaining the compound of formula (IV), which may be converted into selenomethionine. For example, the object of the invention is also the use of the compound of formula (II) as defined earlier, or of its enantiomers, as sources of selenomethionine, and/or selenium in humans or in animals.

By this, is notably meant the use of said compound of formula (II) as:
  precursors of L(+)-selenomethionine either directly or after enzymatic hydrolysis, oxidation and transamination in vivo;
  or as:
  sources of selenium, with the purpose of compensating partial or total selenium deficiency;
  or as
  food ingredients, complements or additives for making nutritional compositions for animal feed (more particularly for cattle, sheep, pigs, horses, cats and dogs as well as poultry).

The examples which follow are simply provided as an illustration and cannot by any means limit the scope of the invention.

EXAMPLE 1

Preparation of 2-hydroxy-4-(methylseleno)butyro-nitrile

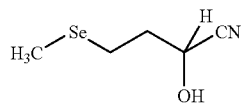

468 mg (3.1 mmol) of 3-methylselenopropionaldehyde (R. Dieden et L. Hevesi, Synthesis 1988, 616-619) are added to a solution of 291 mg (2.8 mmol) of sodium bisulphite in 1.2 mL of water. The mixture is energetically stirred for 10 min at room temperature, and then 155 mg (3.16 mmol) of sodium cyanide are added. After 2 hrs of stirring at room temperature, 5 mL of dichloromethane are added and the organic phase is decanted. The aqueous phase is extracted a second time with 5 mL of dichloromethane. The organic phases are collected, and then after drying (Na$_2$SO$_4$), filtration and evaporation, the desired compound is obtained as a colourless oil, which may be used as such in the following step.

R$_f$ (SiO$_2$, cyclohexane/ethyl acetate, 50/50): 0.22.

RMN-$^1$H (CDCl$_3$, 300 MHz):

δ (ppm)=2.06 (s, 3H); 2.27 (m, 2H); 2.73 (m, 2H); 3.20 (bs, 1H, OH); 4.74 (t, J=8 Hz, α-H).

MS (IE, 70 eV): m/z (%)=179 (80, M+); 164(90); 153 (100); 123(50); 109 (80).

EXAMPLE 2

Preparation of D,L-2-hydroxy-4-methylseleno-butyric acid by hydrolysis of 2-hydroxy-4-(methylseleno)-butyronitrile

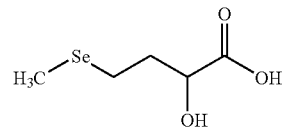

390 mg (2.1 mmol) of the compound described in Example 1 are added to a mixture of 1.7 mL of concentrated hydrochloric acid and 3.6 mL of water. The mixture is heated with reflux for 6 hrs, and then stirred for 14 hrs at room temperature. Next, the aqueous phase is extracted with 3×10 mL of tertbutylmethyl ether. After drying (Na$_2$SO$_4$), filtration and evaporation, the desired compound is obtained as an oil which cold-crystallizes.

R$_f$ (SiO$_2$, cyclohexane/ethyl acetate, 50/50+1% CF$_3$COOH): 0.26.

RMN-$^1$H (CDCl$_3$, 300 MHz):

δ (ppm)=2.02 (s, 3H, SeCH$_3$); 2.08 (m, 1H); 2.22 (m, 1H); 2.70 (m(sym.), 2H); 4.41 (dd, J=8 Hz, J=4 Hz, 1H, α-H).

EXAMPLE 3

Preparation of D,L-2-hydroxy-4-methylseleno-butyric acid amide

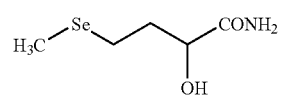

262 mg (1.47 mmol) of 2-hydroxy-4-(methylseleno)-butyronitrile, described in Example 1, are added to a mixture of 0.13 mL of water and 0.5 mL of concentrated sulphuric acid. The mixture is heated to 45° C. for 2 hrs, and then 5 mL of water and 5 mL of dichloromethane are added. The organic phase is decanted, and the aqueous phase is extracted a second time in 5 mL of dichloromethane. The organic phases are collected, and then after drying (Na$_2$SO$_4$), filtration and evaporation, 48 mg of the desired compound are obtained as a viscous colourless oil.

R$_f$ (SiO$_2$, cyclohexane/methanol, 90/10): 0.13.

RMN-$^1$H (CDCl$_3$, 300 MHz):

δ (ppm)=2.06 (s, 3H, SeCH$_3$); 2.08 (m, 1H); 2.30 (m, 1H); 2.75 (m(sym.), 2H); 3.25 (bs, 1H, OH); 4.36 (dd, J=8 Hz, J=4 Hz, 1H, α-H); 5.5 (bs, 1H, NH$_2$); 6.5 (bs, 1H, NH$_2$).

MS (IC, NH): m/z (%)=215 (40, M+NH$_4$)$^+$; 198 (100, M+H)$^+$; 181(20); 102 (25).

EXAMPLE 4

Preparation of a Mixture According to the Invention

Step A: Preparation of the mixture of 2-hydroxy-4-(methyl thio)-butyronitrile and of 2-hydroxy-4-(methylseleno)-butyronitrile

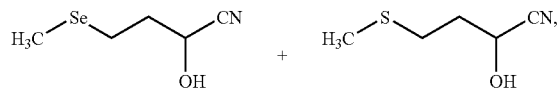

120 mg (0.8 mmol) of 3-methylseleno-propionaldehyde (R. Dieden and L Hevesi, Synthesis 1988, 616-619) and 273 mg (2.5 mmol) of 3-methylthio-propionaldehyde are added to a solution of 312 mg (3 mmol) of sodium bisulphite in 1.2 mL of water. The mixture is energetically stirred for 10 min, at room temperature, and then 164 mg (3.3 mmol) of sodium cyanide are added. After 2 hrs of stirring at room temperature, 5 mL of dichloromethane are added and the organic phase is decanted. The aqueous phase is extracted a second time in 5 mL of dichloromethane. The organic phases are collected, and then after drying ($Na_2SO_4$), filtration and evaporation, the mixture of 2-hydroxy-4-(methylthio)-butyronitrile and 2-hydroxy-4-(methylseleno)butyronitrile is obtained in proportions of 3:1, as a yellowish oil which may be used as such in the next step.

RMN-$^1$H (CDCl$_3$, 300 MHz):

δ (ppm)=2.06 (s, SeCH$_3$); 2.16 (s, SCH$_3$), 2.10-2.35 (m); 2.50-2.65 (m); 2.64-2.90 (m); 3.20 (bs, OH); 4.74 (t, J=8 Hz, 2-H, Se compound); 4.76 (t, J=8 Hz, 2-H, S compound).

Step B: Preparation of the mixture of D,L-2-hydroxy-4-methylselenobutyric acid and of D,L-2-hydroxy-4-methyl-thiobutyric acid 105 mg of the product described in step A, are added to a mixture of 0.6 mL of concentrated hydrochloric acid and 1.3 mL of water. The mixture is heated with reflux for 5 hrs, and then the aqueous phase is extracted with 2×10 mL of tertbutylmethyl ether. After drying (Na$_2$SO$_4$), filtration and evaporation, the mixture of 2-hydroxy-4-(methylthio)butyric acid and of 2-hydroxy-4(methylseleno)butyric acid in proportions of 3:1, is obtained as a yellowish oil.

ES (LC-MS): t$_R$=1.69 min.: 148.9 (M[C$_5$H$_{10}$O$_3$S]—H$^+$);

t$_R$=2.24 min.: 196.8 (M[C$_5$H$_{10}$O$_3$Se]—H$^+$).

EXAMPLE 5

Preparation of Compositions According to the Invention

EXAMPLE 5.A

Gelatine Capsules were Prepared in a Standard Way According to the Following Composition

| | |
|---|---|
| L-2-hydroxy-4-methylselenobutyric acid | 0.2 mg |
| L-2-hydroxy-4-methylthiobutyric acid | 200 mg |
| Excipients* and encapsulation** | qsp a gelatin capsule of 1000 mg |

(*maize starch, lactose, magnesium stearate, sodium lauryl sulphate,
**gelatin, titanium dioxide, colouring agents).

EXAMPLE 5.B

Gelatine Capsules were Prepared in a Standard Way According to the Following Composition

| | |
|---|---|
| L-2-hydroxy-4-methylselenobutyric acid | 0.05 mg |
| L-2-hydroxy-4-methylthiobutyric acid | 50 mg |
| Excipients* and encapsulation** | qsp a gelatin capsule of 1000 mg |

(*maize starch, lactose, magnesium stearate, sodium lauryl sulphate,
**gelatin, titanium dioxide, colouring agents).

EXAMPLE 5.C

Gelatine Capsules were Prepared in a Standard Way According to the Following Composition

| | |
|---|---|
| L-2-hydroxy-4-methylselenobutyric acid | 10 mg |
| L-2-hydroxy-4-methylthiobutyric acid | 10 g |
| Water | qsp 1000 mL |

The invention claimed is:

1. A method for preparing 2-hydroxy-4-methylseleno-butyric acid, comprising the steps of:

reacting 3-methylselenoproprionaldehyde of formula (I):

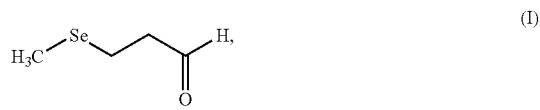

with an alkaline cyanide of formula M$^+$CN$^-$, M representing an alkaline metal atom, in a polar protic solvent, to form 2-hydroxy-4-methylselenobutyro-nitrile, a compound of formula (II):

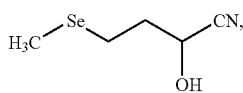
(II)

and
hydrolyzing the compound of formula (II) in a hot strongly concentrated acid medium, in a polar protic solvent, to form a compound of formula (IV):

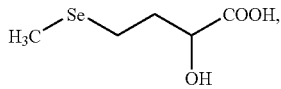
(IV)

which may optionally be transformed into one of its salts after addition with a physiologically acceptable base.

2. The preparation method according to claim 1, wherein the hydrolyzing comprises hydrolyzing the compound of formula (II) in a hot concentrated sulphuric acid medium in a polar protic solvent, to form a compound of formula (III):

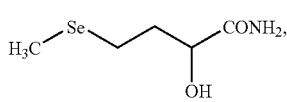
(III)

and
hydrolyzing the compound of formula (III) in a hot strongly concentrated acid medium to form the compound of formula (IV).

3. The method according to claim 1, wherein the alkaline cyanide is selected from sodium cyanide, potassium cyanide, and lithium cyanide.

4. The preparation method according to claim 1, wherein the polar protic solvent is water.

5. A method for preparing a mixture of 2-hydroxy-4-methylselenobutyric acid and of 2-hydroxy-4-methylthiobutyric acid, comprising the steps of:
reacting a mixture of 3-methylseleno-proprionaldehyde of formula (I), and of 3-methyl-thioproprionaldehyde of formula (Ia):

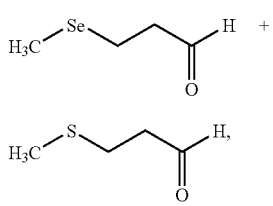
(I)

(Ia)

with an alkaline cyanide of formula $M^+CN^-$, M representing an alkaline metal atom, in a polar protic solvent, to form the mixture of 2-hydroxy-4-methylselenobutyronitrile of formula (II) and of 2-hydroxy-4-methylthiobutyronitrile of formula (IIa):

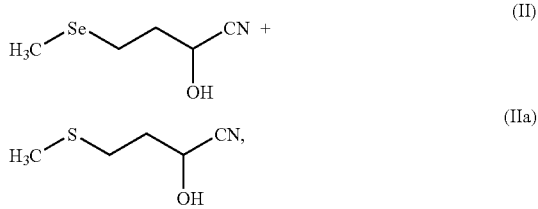
(II)

(IIa)

and
hydrolyzing compounds (II) and (IIa) in a hot strongly concentrated acid medium, in a polar protic solvent, to form the mixture of two compounds of formulae (IV) and (IVa):

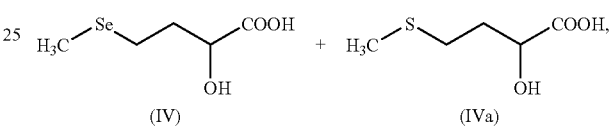
(IV)        (IVa)

which may optionally be transformed into a mixture of their salts after addition with a physiologically acceptable base, wherein the relative proportion of both compounds (IV) and (IVa) are set from the beginning of the method by the relative amounts of compounds (I) and (Ia), and are retained all along said preparation method.

6. The method according to claim 5, wherein the alkaline cyanide is selected from sodium cyanide, potassium cyanide and lithium cyanide.

7. The preparation method according to claim 5, wherein the polar protic solvent is water.

8. The preparation method according to claim 5, wherein the ratio between the compound (IV) and the compound (IVa) varies between 0.01% and 1.0% by weight.

9. The preparation method according to claim 8, wherein the ratio between the compound (IV) and the compound (IVa) varies between 0.05% and 0.5% by weight.

10. The method according to claim 1, wherein said reacting step is in the presence of an alkaline bisulphite salt of formula $M^+HSO_3^-$.

11. The method according to claim 5, wherein said reacting step is in the presence of an alkaline bisulphite salt of formula $M^+HSO_3^-$.

* * * * *